United States Patent

Tojo et al.

[11] Patent Number: 5,866,141
[45] Date of Patent: Feb. 2, 1999

[54] PATCH PREPARATIONS FOR TREATING PLANTS

[75] Inventors: Kakuji Tojo, Iizuka; Yuzuru Wada, Tokyo; Yuichi Otsu, Tochigi; Kunihiro Isono, Shimotsuga-gun; Shinzaburo Sone, Ibaraki; Katsuhiko Hanaki, Oyama, all of Japan

[73] Assignee: Nihon Bayer Agrochem K.K., Tokyo, Japan

[21] Appl. No.: 610,789

[22] Filed: Mar. 11, 1996

[30] Foreign Application Priority Data

Mar. 15, 1995 [JP] Japan .................................. 7-081994

[51] Int. Cl.$^6$ ...................................................... A61K 9/70
[52] U.S. Cl. .......................... 424/400; 424/405; 424/408
[58] Field of Search ..................... 424/405, 408, 424/400

[56] References Cited

U.S. PATENT DOCUMENTS

| | | |
|---|---|---|
| 4,291,497 | 9/1981 | Manankov . |
| 4,629,645 | 12/1986 | Inoue . |
| 5,142,817 | 9/1992 | Rolf ............................................ 47/24 |
| 5,201,925 | 4/1993 | Itzel ......................................... 424/448 |
| 5,224,967 | 7/1993 | Rolf et al. .................................. 47/58 |
| 5,343,653 | 9/1994 | Itzel .......................................... 47/1.5 |

FOREIGN PATENT DOCUMENTS

| | | |
|---|---|---|
| 0 254 196 A1 | 1/1988 | European Pat. Off. . |
| 0 290 155 A3 | 11/1988 | European Pat. Off. . |
| 44 16 927 C1 | 8/1995 | Germany . |
| 19506094 | 9/1995 | Germany . |
| 19506095 | 9/1995 | Germany . |
| 2 212 063 | 7/1989 | United Kingdom . |

OTHER PUBLICATIONS

Derwent Abstract of JP–A–63 051 301.
Derwent Abstract J59–142264, Aug. 15, 1984.
Derwent Abstract, J61–104838, May 23, 1986.
Derwent Abstract J7–10708, Jan. 13, 1995.
Abstract of JP–A–58–099 402, filed Jun. 13, 1983.
JP Utility Model Claim Sho 59–178301 and abstract.

*Primary Examiner*—Thurman K. Page
*Assistant Examiner*—D. Faulkner
*Attorney, Agent, or Firm*—Sprung Kramer Schaefer & Briscoe

[57] ABSTRACT

The following invention introduces a patch preparation for treating plants, whereas the patch preparations comprise a chemical layer composed of at least one agrochemically active compound, at least one adhesive and optionally, one or more additives. The components are dispersed in a matrix state on a substrate which are then introduced on the roots of the plant to be treated.

4 Claims, No Drawings

PATCH PREPARATIONS FOR TREATING PLANTS

This application is a continuation of PCI HEI-7-81995 published Mar. 15, 1995

The present invention relates to new patch preparations for treating plants.

There are two application methods, which hitherto have been mostly employed for administering agrochemicals to plants.

The first method comprises applying the active ingredients by spraying liquid formulations or solid formulations in finely pulverized form onto the surface of the plants to be treated. The second method consists in mixing liquid or solid formulations of active ingredients with the soil in the vicinity of the roots of the plants to be treated.

When working according to the spraying technique, the sprayed agrochemicals reach the place of activity at a fast rate, which means that this method is a fast acting one. However, a disadvantage of this method is that the major part of the sprayed chemicals generally is dripping down and deposits on the soil or is drifting away from the area to be treated, thus leaving a rather low dosage of the active ingredients on the plants. Further, there is a risk that the operators, who are spraying the formulations, become exposed to the chemicals during spraying the formulations.

Upon working according to the second of the two above-mentioned methods, i.e. mixing formulations with the soil, the risk of becoming contaminated is markedly reduced for the operators, who are applying the formulations. However, this method suffers from the disavantage that the desired effect can only be achieved, if the chemicals used in the treatment have systemic properties and are able to penetrate into the plants and to be translocated therein. Compared with the application by means of spraying, the mixing technique has the demerits that the biological effect of the active ingredients emerges at a slower pace, the effective amounts of the active ingredients in the treatment are lower due to absorption of the active ingredients in the soil and due to being washed out by irrigation, and a higher risk of a prolonged residual toxicity in the soil is inherent.

Considering the above-said, it is highly desirable to develop a novel control technique avoiding the disadvantages of the above-mentioned conventional methods for combating pests by using the active ingredients in an amount as low as possible and still maintaining a biological effect as high as possible.

As a result of extensive research to resolve the above problems, there have been found now new patch preparations for treating plants.

Thus, the present invention provides patch preparations for treating plants, which patch preparations comprise a chemical layer composed of at least one agrochemically active compound, at least one adhesive and optionally, one or more additives, said components being dispersed in a matrix state on a substrate.

It is also an object of the present invention to apply agrochemicals to plants by attaching to the surface of the plants patch preparations comprising a chemical layer composed of at least one agrochemically active compound, at least one adhesive and, optionally, one or more additives, said components being dispersed in a matrix state on a substrate.

It is decidedly surprising that the patch preparations according to the invention are outstandingly effective for applying agrochemicals to plants, since it could not be foreseen that the preparations are suitable for causing a sufficient penetration of the active ingredients into the plants.

When the patch preparations according to the invention are attached to plants, the compositions ensure a sufficient application of the agrochemicals to the plants to achieve the desired effect, even if the active compounds are used in a far lower amount than that to be used in the conventional spray application. A particular advantage of the patch preparations is that the agrochemicals can be applied in exactly the dosage required, that the active ingredients are persistently released and that no chemicals are wasted. Further the preparations guarantee an effective control and do almost completely eliminate an undesired release of the active compounds to the environment. After all, there is no risk for the operators of becoming exposed to dusts or sprays of chemicals. Thus, the present invention provides epoch-making formulations having a high-grade safety.

The patch preparations according to the invention do comprise one or more agrochemically active compounds, such as pesticidally active compounds, microbicidally active compounds, plants growth regulants and so on. Pesticidal compounds in the present context are compounds which are suitable for the control of insects, acarides (mites), nematodes etc. infesting plants. Microbicidal compounds in the present context are fungicides or bactericides, i.e. compounds which are suitable for combating fungi and/or bacteriae infecting plants. Plant growth regulants in the present context are compounds, which interfere with the plant metabolism in a desired mode without damaging the plant. Such growth regulants, for example, may cause a promotion of growth, a retardation of growth, regulation of flowering, induction of parthenocarpy etc.. The formulations according to the invention may comprise any of such afore-mentioned agrochemicals having systemic properties.

As examples of pesticidal compounds, which can preferably be present in the patch preparations according to the invention, there may be mentioned:

1-(6-chloro-3-pyridylmethyl)-N-nitro-imidazolidin-2-ylideneamine, N-cyano-N-(2-chloro-5-pyridylmethyl)-N'-methyl-acetamidine, 1-[N-(6-chloro-3-pyridylmethyl)-N-ethyl-amino]-1-methylamino-2-nitroethylene, 1-(2-chloro-5-pyridylmethyl)-3,5-dimethyl-2-nitroimino-hexahydro-1,3,5-triazine, 1-(2-chloro-5-thiazolylmethyl)-3,5-dimethyl-2-nitroimino-hexahydro-1,3,5-triazine, 1-(2-chloro-5-thiazolylmethyl)-3-methyl-2-nitroguanidine, O,O-dimethyl-O-3-methyl-4-(methylsulfinyl)-phenylphos-phorothioate, trans-1,4,5,6-tetrahydro-1-methyl-2-[2-(3-methyl-2-thienyl)-vinyl]-pyrimidine tartrate, and (−)-(s)-2,3,5,6-tetrahydro-6-phenylimidazo-[2,1-b]thiazole hydrochloride.

As examples of fungicidal compounds, which can preferably be present in the patch preparations according to the invention, there may be mentioned:

1-(4-chlorophenoxy)-3,3-dimethyl-1-(1,2,4-triazol-1-yl)-2-butanone, all-rac-1-(biphenyl-4-yloxy)-3,3-dimethyl-1-(1H-1,2,4-triazol-1-yl)-butan-2-ol, 2-p-chlorophenyl-2-(1H-1,2,4-triazol-1-ylmethyl)-hexanenitrile, (RS)-2-(2,4-dichlorophenyl)-1-(1H-1,2,4-triazol-1-yl)-hexan-2-ol, 1-[2-(2,4-dichlorophenyl)-4-propyl-1,3-dioxolane-2-ylmethyl]-1H-1,2,4-triazole, (E)-4-chloro-α,α,α-trifluoro-N-(1-imidazol-1-yl-2-propoxyethylidene)-0-toluidine, N-propyl-N-[2-(2,4,6-trichlorophenoxy)-ethyl]-imidazol-1-ylcarboxyamide, pent-4-enyl N-furfuryl-N-imidazol-1-ylcarbonyl-DL-homoalaninate, 2,4'-dichloro-α-(pyrimi din- 5-yl)-benzhydrylalcohol, (E)-(RS)-1-(4-chlorophenyl)-4,4-dimethyl-2-(1H-1,2,4-triazol-1-yl)-1-penten-3-ol, (E)-(S)-1-(4-chlorophenyl)-4,4-dimethyl-2-(1H-1,2,4-triazol-1-yl)-pent-1-en-3-ol, (RS)-1-(4-chlorophenyl)-4,4-dimethyl-3-(1H-1,2,4-triazol-1-ylmethyl)-pentan-3-ol, 2',4'-dichloro-2-(3-pyridyl)-acetophenone-(EZ)-O-methyloxime, 1,4-bis-(2,2,2-trichloro-1-formamidoethyl)-piperazine, (2RS, 3RS)-1-(4-chlorophenyl)-4,4-dimethyl-2-(1H-1,2,4-triazol-1-yl)-pentan-3-ol, (±)-cis-4-[3-(4-tert-butylphenyl)-2-methylpropyl]-2,6-dimethylmorpholine and 2-(4-fluorophenyl)-2-(1,2,4-triazol-2-ylmethyl)-3-(2-chlorophenyl)-epoxyethane.

As examples of plant growth regulants, which can preferably be present in the patch preparations according to the invention, there may be mentioned:

2-chloroethylphosphonic acid, indolebutyric acid, sodium 5-chloro-3(1H)-indazolylacetate, ethyl 5-chloro-3(1H)-indazolylacetate, sodium 4-chloro-2-hydroxymethylphenoxyacetate, triethanolamine (±)-2-(2,4-dichlorophenoxy)-propionic acid, α-naphthylacetamide, p-chlorophenoxyacetic acid, 6-(N-benzylamino)-purine, 1-(2-chloro-4-pyridyl)-3-phenylurea, gibberellin, maleic hydrazide, α-cyclopropyl-α-(4-methoxyphenyl)-5-pyrimidinemethanol, 4'-chloro-2'-(α-hydroxybenzyl)-isonicotinanilide, (E)-(S)-1-(4-chlorophenyl)-4,4-dimethyl-2-(1H-1,2,4-triazol-1-yl)-pent-1-en-3-ol, 2-chloroethyltrimethylammonium chloride, (2RS, 3RS)-1-4 (4-chlorophenyl)-4,4-dimethyl-2-(1H-1,2,4-triazol-1-yl) pentan-3-ol, 1,1-dimethylpiperidinium chloride and N-(dimethylamino)-succinamide.

However, the above-mentioned examples do in no way limit the agrochemically active compounds, which can be used in the patch preparations according to the invention.

The patch preparations according to the invention do contain at least one adhesive. Such adhesives are preferably selected from (a) natural-type adhesives, such as starch, hide glue, casein, dextrin, vegetable gum, animals and plants protein, shellac, natural rubber, sodium silicate, etc.;

(b) thermoplastic-type adhesives such as alkyd, acrylic ester, polyamide, polystyrene, synthetic rubber, polyvinylalcohol, etc.; and (c) thermosetting-type adhesives such as urea resin, phenolic resin, unsaturated polyester resin, epoxy resin, melamine resin, furan resin, alkyd resin, etc.

These adhesives can be used alone or in combination with two or more of them.

Particularly preferred adhesives are those composed of natural rubber or acrylic ester-type resin.

The patch preparations according to the invention do contain a substrate overlaying the chemical layer comprising the agrochemically active compound(s), the adhesive(s) and, optionally, the additive(s). Such substrates can be, for example, films or non-woven sheets made of synthetic resins, such as polyethylene terephthalate, polyethylene, polypropylene and polyvinyl chloride. Among them, the films made of polyethylene terephthalate are preferred. However, the materials of the substrate used in the patch preparations according to the invention are in no way restricted to the above-mentioned ones. Other polymeric materials, such as paper and the like can also be used.

The chemical layer of the patch preparations according to the invention can optionally contain one or more additives, such as surface-active agents, solvents and accelerators for expediting the release of the agrochemically active substances.

As examples of accelerators for enhancing the release of the agrochemicals, there may be mentioned p-menthane derivatives, such as menthol and limonene.

As examples of surface-active agents, there may be mentioned polyoxyethylene alkylethers, polyoxyethylene alkylphenylethers, polyoxyethylene alkylphenylether formaldehyde condensates, polyoxyethylene-polyoxypropylene block polymers, polyoxyethylene-polyoxypropylene block polymer alkyl phenyl ethers, sorbitan fatty acid esters, polyoxyethylene fatty acid esters, polyoxyethylene sorbitan fatty acid esters, polyoxyethylene castor oil ethers, etc.

As solvents there can be used all organic diluents, which are customarily applied in formulations of agrochemicals. Preferred solvents are aliphatic, alicyclic or aromatic hydrocarbons, such as hexane, cyclohexane, toluene and xylene, and also halogenated hydrocarbons, such as chloroform.

The patch preparations according to the invention can be prepared by conventional methods. Thus, they can be prepared by adding a solution of the agrochemical(s) optionally in admixture with additive(s), in an organic solvent to the adhesive(s), spreading the resulting mixture on a film of the substrate, and evaporating the solvent partly or completely followed by sealing the chemical layer with a protective film.

The process mentioned above is merely one embodiment for preparing patch preparations according to the invention. The present invention is therefore in no way restricted to the above embodiment, and various modifications and changes thereof can be made.

The concentrations of the components in the chemical layer of the patch preparations according to the invention can be varied within a relatively wide range. In general, the layer comprises from about 1 to about 50 parts by weight, preferably from about 2 to about 25 parts by weight of one or more agrochemicals per 100 parts by weight of the layer, and from about 40 to 95 parts by weight, preferably from about 55 to 70 parts by weight of one or more adhesives per 100 parts by weight of the layer. The concentrations of the additives may also be varied within a relatively wide range. In general, the layer comprises from 0 to about 45 parts by weight, preferably from 0 to about 35 parts by weight of one or more additives per 100 parts by weight of the layer. Thus, the layer can contain from about 1 to about 40 parts by weight, preferably from about 5 to about 30 parts by weight of one or more accelerators for releasing the agrochemical (s), and from 0 to about 6 parts by weight, preferably from 0 to about 5 parts by weight of one or more surface-active agents optionally in admixture with one or more solvents.

In case of actually using patch preparations according to the invention, there are applied patch preparations, which have been prepared by cutting films or sheets of such preparations into pieces having the desired size before using them, or by adjusting the shape of the preparations to the desired size in advance. The protective seal on the chemical layer of the preparations is removed, and then they are sticked to the surface of the plants at stem portions and or xylems in such a manner that the chemical layer comes into contact with the plant.

The size of the patch preparations can appropriately be varied depending on the purpose of plant treatment, the size of a target plant, the situation of the portions at which the patch preparations are sticked, and the like.

The patch preparations according to the invention can be used for combating all kinds of animal pests, which can be controlled with the pesticidal compounds in the chemical layer. Specific examples of such pests include the following:

(1.) Coleptera, such as

Callosobruchus Chinensis (adzuki bean weevil),
Sitophilus zeamais (maize weevil),
Tribolium castaneum (red flour beetle),
Epilachna vigintioctomaculata (large 28-spotted lady beetle),
Agriotes fuscicollis (barley wireworm),
Anomala rufocuprea (soybean beetle),
Leptinotarsa decemlineata. Diabrotica spp., Monochamus alternatus (Japanese pine sawyer),
Lissorhoptrus oryzophilus (rice water weevil),
Lyctus bruneus (powderpost beetle), etc.

2. Lepidoptera, such as

Lymantria dispar (gypsy moth),
Malacosoma neustria, Pieris rapae, Spodoptera litura (common cutworm),
Mamestra brassicae (cabbage armyworm),
Chilo suppressalis (Asiatic rice borer),
Pyrausta nubilalis (oriental corn borer),
Ephestia cautella, Adoxophves orana (smaller tea tortrix),
Carpocapsa pomonella, Agrotis fucosa (cutworm),
Galleria mellonella (greater wax moth),
Plutella maculipennis (diamondback moth),
Heliothis virescens, Phyllocnistis citrella, etc.

3. Hemiptera, such as

Nephotettix cincticeps (green rice leafhopper),
Nilaparvata luaens (brown rice planthopper),
Pseudococcus comstocki (Comstock mealyburg),
Unaspis yanonensis (arrowhead scale),
Myzus persicae (green peach aphid),
Aphis pomi (green apple aphis),
Aphis gossypii (cotton aphid),
Rhopalosiphum pseuddobrassicas (turnip aphid),
Stephanitis nashi (pear lace bug),
Nazara spp., Cimex lectularius, Trialeurodes vaporariorum (greenhouse whitefly),
Psylla spp. (jumping plantlice), etc.

(4) Orthoptera, such as

Blatella germanica (German cockroach),
Periplaneta americana (American cockroach),
Gryllotalpa africana (mole cricket),
Locusta migratoria migratoriodes, etc.

(5) Isoptera, such as

Reticulitermes speratus (Japanese white birch aphid),
Coptotermes formosanus (Formosan subterranean termite), etc.
Thysanoptera, such as
Thrips palmi karny.

(6) Diptera, such as

Musaca domestica (oriental house fly),
Aedes aegypti, Hylemia platura (seed-corn maggot),
Culex pipiens, Anopheles sinensis, Culex tritaeniorhynchus, etc.

(7) Acarina, such as

Tetranychus telarius (carmine spider mite),
Tetranychus urticae (tow-spotted spider mite),
Panonychus citri (citus red mite),
Aculops pelekassi (pink citrus rust mite),
Tarsonemus spp. (tarsonemid mites), etc., and (8) Nematoda, such as Meloidogyne incognita (southern root-knot nematode)
Bursaphelenchus lignicolus mamiya et kiyohara,
Aphelenchoides besseyi (rice white-tip nematode),
Heterodera glycines (soybean cyst nematode),
Pratylenchus spp. (root-lesion nematode), etc.

The patch preparations according to the invention can also be used for the control of all kinds of microbicidal plant diseases, which can be combated with the microbicidal compounds in the chemical layer. Specific examples of such microbicidal plant diseases are those caused by Plamodiophoromycetes,
Oomycetes,
Chytridiomycetes,
Zygomycetes,
Ascomycetes,
Basidiomycetes and Deuteromycetes,
Pseudomonadeceae,
Rhizobiaceae,
Enterobacteriaceae,
Corynebateriaceae and Streptomycetaceae, etc.

The patch preparations according to the invention can also be used for growth promotion, growth retardation, regulation of flowering, induction of parthenocarpy and others, by incorporating a plant growth regulator into the chemical layer for the purpose of providing plant regulatory activity.

The target plants to which the patch preparations according to the invention are applicable are not particularly restricted, but as particularly preferred target plants, there may be mentioned fruit vegetables, flowers and ornamental plants and fruit trees. Specifically they may be illustrated by tomato, cucumber, eggplant, rose, chrysanthemum, carnation, tulip, grape, strawberry, etc.

The patch preparations according to the invention, their preparation and their use are illustrated more specifically by the following examples, but the scope of the invention should not be restricted thereto in any way.

EXAMPLES

The agrochemicals tested were:

imidacloprid: 1-(6-chloro-3-pyridylmethyl)-N-nitro-imidazolidin-2-ylideneamine

A-1: N-cyano-N-(2-chloro-5-pyridylmethyl)-N'-methylacet-amidine

Example 1

Production of patch preparations.

A solution of imidachloprid (0.42 mg) in chloroform (5.0 ml) was dissolved in a solution of acrylic adhesive (obtained by mixing a small amount of acrylic acid, methacrylic acid and vinyl acetate to acrylic acid ester followed by copolymerization; solid content 40%) (20 g) in toluene. The resulting mixture was spread on a polyethylene terephthalate film at room temperature . The coated film was then heated to 60° C. to completely evaporate toluene and chloroform. After evaporation, the suface of the chemical layer was sealed for protection with a polyethylene terephthalatefilm to prepare a patch preparation comprising the active ingredient in a concentration of 5% by weight.

Example 2

Test for insecticidal effectiveness.

The patch preparation prepared according to Example 1 was designated as I.1.

The patch preparation prepared by further adding to the mixture according to Example 1 15% by weight of menthol as accelerator for enhancing the release of the active ingredient was designated as I.2.

The patch preparation prepared by further adding to the mixture according to Example 1 15% by weight of limonene as accelerator for enhancing the release of the active ingredient was designated as I3.

Testing procedure

Crop plants: Eggplants (var. Senryo 2) were used in the six leaf stage. Cucumber (var. Siyo) were used in the four leaf stage.

Pests: *Myzus persicae* (green peach aphid) (line resistant to organic phosphorus pesticide, carbamate pesticide) against eggplants. *Aphis gossypii* (cotton aphid) (field-picking line) against cucumbers Region system: one region one pot, two successive systems Testing procedure The patch preparations were cut into pieces so that each piece contained the active ingredient, i.e. imidachloprid, in an amount of 0,5 mg and 1 mg respectively. One of the pieces was stuck to the stem of each plant body at a hight of 8 cm above the ground. By using aphid chambers, 10 female adults of vivipar non-elytroptera were applied immediately after the treatment, 7 days, 14 days and 21 days after the treatment. The number of the surviving female adults of vivipar non-elytroptera and the number of larvae produced by the applied female adults of vivipar non-elytroptera were examined 4 days after the inoculation. Furthermore, all of the aphids which had been translocated from the nearby breeding origins to the treated stocks were examined 25 days after the treatment.

Simultaneously with above, phytotoxicity was determined and the evaluation was conducted according to the following criteria:

0: no phytotoxicity is observed.

1: slight withering of leaf margins and brown spots in leaves are observed.

2: distinct withering of leaf margins and brown spots in leaves are observed.

3: even for new leaves, distinct withering of leaf margins and brown spots in leaves are observed.

4: even for new leaves, phytotoxicity is observed and growth inhibition is also observed.

5: dead insecticidal rate (%) =

$$\left(1 - \frac{\text{Number of surviving insects in treated region}}{\text{Number of surviving insects in non-treated region}}\right) \times 100$$

Test results are shown in Tables 1 and 2

(Table 1: eggplant test; Table 2: cucumber test).

TABLE 1

(Eggplant Test)

| | | insecticidal rate (%) | | | | | | | | | |
|---|---|---|---|---|---|---|---|---|---|---|---|
| | amount of active ingredient | inoculation 0 day after treating | | 7 days | | 14 days | | 21 days | | phytotoxicity | |
| patch preparation | mg/plant | A | N | A | N | A | N | A | N | 25 days | 25 days |
| I.1 | 1 | 73 | 91 | 100 | 100 | 98 | 100 | 93 | 97 | 94 | 0 |
|  | 0.5 | 80 | 92 | 94 | 100 | 75 | 84 | 83 | 80 | 84 | 0 |
| I.2 | 1 | 93 | 100 | 100 | 100 | 100 | 100 | 100 | 100 | 100 | 0 |
|  | 0.5 | 90 | 100 | 100 | 100 | 100 | 100 | 95 | 98 | 95 | 0 |
| I.3 | 1 | 93 | 99.5 | 100 | 100 | 98 | 100 | 93 | 95 | 92 | 0 |
|  | 0.5 | 65 | 99 | 100 | 98 | 85 | 85 | 88 | 75 | 71 | 0 |
| non-treatment | — | 0 | 0 | 0 | 0 | 0 | 0 | 0 | 0 | 0 | 0 |
| number of larvae per chamber |  |  |  | 50.8 |  | 21.8 |  | 43 |  | 26.3 |  |
| number of all aphids per plant |  |  |  |  |  |  |  |  |  | 412.5 |  |

(Notes)
A: effect against adults
B: effect against larvae

TABLE 2

(Cucumber Test)

| | | insecticidal rate (%) | | | | | | | | | |
|---|---|---|---|---|---|---|---|---|---|---|---|
| | amount of active ingredient | inoculation 0 day after treating | | 7 days | | 14 days | | 21 days | | phytotoxicity | |
| patch preparation | mg/plant | A | N | A | N | A | N | A | N | 25 days | 25 days |
| I.1 | 1 | 95 | 100 | 88 | 99 | 63 | 64 | 28 | 35 | 94 | 0 |
|  | 0.5 | 95 | 100 | 53 | 67 | 58 | 71 | 5 | 8 | 91 | 0 |
| I.2 | 1 | 100 | 100 | 80 | 97 | 78 | 98 | 38 | 43 | 99.8 | 0 |

TABLE 2-continued (Cucumber Test)

| patch preparation | amount of active ingredient mg/plant | inoculation 0 day after treating | | 7 days | | 14 days | | 21 days | | 25 days | phytotoxicity 25 days |
|---|---|---|---|---|---|---|---|---|---|---|---|
| | | A | N | A | N | A | N | A | N | | |
| | 0.5 | 98 | 100 | 75 | 97 | 58 | 79 | 8 | 16 | 97 | 0 |
| 1.3 | 1 | 100 | 100 | 65 | 81 | 70 | 92 | 3 | 19 | 97 | 0 |
| 0.5 | 98 | 100 | 53 | 78 | 73 | 69 | 0 | 8 | 96 | 0 | |
| non-treatment | — | 0 | 0 | 0 | 0 | 0 | 0 | 0 | 0 | 0 | 0 |
| number of larvae per chamber | | | 55.5 | | 50.5 | | 26.3 | | 48.5 | | |
| number of all aphids per plant | | | | | | | | | | 255 | |

Note:
A and N have the same meanings as in Table 1.

Example 3

A patch preparation, the chemical layer of which consists of 18 parts by weight of imidacloprid and 82 parts by weight of acrylic adhesive, is prepared in the same manner as in Example 1.

Example 4

A patch preparation, the chemical layer of which consist of 5 parts by weight of the compound A-1 and 95 parts by weight of acrylic adhesive, is prepared in the same manner as in Example 1.

Example 5

A patch preparation, the chemical layer of which consists of 15 parts by weight of imidacloprid, 55 parts by weight of acrylic adhesive and 30 parts by weight of menthol, is prepared in the same manner as in Example 1.

It will be understood that the specification and examples are illustrative but not limitative of the present invention and that other embodiments within the spirit and scope of the invention will suggest themselves to those skilled in the art.

We claim:

1. A patch preparation for treating plants which patch preparation comprises a chemical layer composed of the following components imidacloprid, at least one adhesive, and at least one additive, said components being dispersed in a matrix state on a substrate, wherein said substrate is selected from the group consisting of polyethylene terephthalate, polyethylene, polypropylene, or polyvinyl chloride; and wherein said additive is selected from the group consisting of surface-active agents, solvents, and accelerators for expediting the release of the imidacloprid.

2. A method for applying agrochemicals to plants, which method comprises attaching to the surface of the plant a patch preparation according to claim 1.

3. A patch preparation for treating plants, which patch preparation comprises a chemical layer composed of the following components at least one agrochemically active compound selected from the group consisting of 1-(6-chloro-3-pyridylmethyl)-N-nitro-imidazolidin-2-ylideneamine, N-cyano-N'-(2-chloro-5-pyridylmethyl)-N'-methylacetemidine and 1-[N-(6chloro-3-pyridylmethyl)-N-ethylamino]-1-methylamino-2-nitroethylene;

at least one adhesive selected from the group consisting of starch, hide glue, casein, dextrin, vegetable gum, animals and plants protein, shellac, natural rubber and sodium silicate, allyd, acrylic esters, polyamide, polystyrene, synthetic rubber and polyvinylalcohol, urea resins, phenolic resins, unsaturated polyester resins, epoxy resins, melamine resins, furan resins and alkyd resins, and optionally, one accelerator for expediting the release of the agrochemically active compound, said accelerator being selected from the group consistinglof p-menthane derivatives, said components being dispersed in a matrix state on a substrate.

4. A method for applying agrochemicals to plants, which method comprises attaching to the surface of the plant a patch preparation according to claim 3.

* * * * *